United States Patent
Bagwell et al.

(10) Patent No.: US 10,149,474 B2
(45) Date of Patent: Dec. 11, 2018

(54) HERBICIDAL COMPOSITIONS COMPRISING ISOXAFLUTOLE AND DIFLUFENICAN

(71) Applicant: BAYER CROPSCIENCE AKTIENGESELLSCHAFT, Monheim am Rhein (DE)

(72) Inventors: Ralph Bagwell, Chapel Hill, NC (US); Herve Tossens, Verlaine (BE); Martin Jeffrey Hills, Idstein (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/559,396

(22) PCT Filed: Mar. 15, 2016

(86) PCT No.: PCT/EP2016/055485
§ 371 (c)(1),
(2) Date: Sep. 18, 2017

(87) PCT Pub. No.: WO2016/150751
PCT Pub. Date: Sep. 29, 2016

(65) Prior Publication Data
US 2018/0070592 A1     Mar. 15, 2018

(30) Foreign Application Priority Data

Mar. 20, 2015   (EP) .................................. 15160008

(51) Int. Cl.
*A01N 43/80*     (2006.01)
*A01N 43/40*     (2006.01)

(52) U.S. Cl.
CPC ............. *A01N 43/80* (2013.01); *A01N 43/40* (2013.01); *A01N 2300/00* (2013.01)

(58) Field of Classification Search
CPC ..... A01N 43/80; A01N 43/40; A01N 2300/00
See application file for complete search history.

(56) References Cited

U.S. PATENT DOCUMENTS 4,618,366 A * 10/1986 Cramp ................... A01N 43/40
                                                               504/255
6,214,770 B1    4/2001 Millet et al.
2004/0058427 A1 * 3/2004 Andrews .............. C12N 9/0069
                                                               435/196

FOREIGN PATENT DOCUMENTS

EP         0527036 A1 * 2/1993 ............. A01N 43/80
WO       00/78147 A1    12/2000

OTHER PUBLICATIONS

"The Pesticide Manual", 15th edition, The British Crop Protection Council and the Royal Soc. of Chemistry, 2009, S.362ff.
"The Pesticide Manual", 15th edition, The British Crop Protection Council and the Royal Soc. of Chemistry, 2009, S.680ff.
International Search Report of International Patent Application No. PCT/EP2016/055485 dated Apr. 20, 2016.

* cited by examiner

*Primary Examiner* — John Pak
*Assistant Examiner* — Andriae M Holt
(74) *Attorney, Agent, or Firm* — McBee Moore Woodward & Vanik IP, LLC

(57) ABSTRACT

A description is given of herbicidal compositions which comprise the active ingredients isoxaflutole and diflufenican. These herbicidal compositions are particularly suitable for use against weed plants in crops of useful plants.

10 Claims, No Drawings

HERBICIDAL COMPOSITIONS COMPRISING ISOXAFLUTOLE AND DIFLUFENICAN

CROSS-REFERENCE TO RELATED APPLICATIONS

This application is a National Stage entry of International Application No. PCT/EP2016/055485, filed Mar. 15, 2016, which claims priority to European Patent Application No. 15160008.7, filed Mar. 20, 2015.

BACKGROUND

Field

The present invention relates to agrochemically active herbicidal compositions and also to their use for controlling weed plants.

Description of Related Art

The active ingredient isoxaflutole (IUPAC name: 5-cyclopropyl-1,2-oxazol-4-yl)($\alpha,\alpha,\alpha$-trifluoro-2-mesyl-p-tolyl) methanone) is a known active herbicidal ingredient for controlling unwanted weed plants in maize crops and sugarcane crops preferably pre-emergence; see, for example, "The Pesticide Manual", 15th edition, The British Crop Protection Council and the Royal Soc. of Chemistry, 2009, p. 680. Isoxaflutole inhibits hydroxyphenylpyruvate dioxygenase (HPPD). The active ingredient diflufenican (IUPAC name: 2',4'-difluoro-2-($\alpha,\alpha,\alpha$-trifluoro-m-tolyloxy)nicotinanilide) is a known active herbicidal ingredient for controlling unwanted weed plants pre-emergence and early post-emergence in barley and wheat crops; see, for example, "The Pesticide Manual", 15th edition, The British Crop Protection Council and the Royal Soc. of Chemistry, 2009, p. 362.

A variety of specifications disclose herbicidal compositions comprising isoxaflutole and other herbicides. Thus, for example, U.S. Pat. No. 6,214,770 B1 describes discloses herbicidal compositions comprising isoxaflutole and herbicidally active ureas. These herbicidal compositions extend the weed spectrum for control relative to each of the individual active ingredients, but without producing further possibilities for use, such as deployment in other crops of useful plants, or shifting of the application window. Moreover, these herbicidal compositions known from the prior art do not solve the problem of increasing resistance by weed plants to active herbicidal ingredients from among the HPPD inhibitors, of which isoxaflutole is one.

SUMMARY

It is an object of the present invention, therefore, to provide further herbicidal compositions which permit effective control of unwanted plants in various crops of useful plants within user-friendly time windows.

This object has been achieved the provision of herbicidal compositions comprising isoxaflutole and diflufenican.

The present invention accordingly provides herbicidal compositions comprising
(A) isoxaflutole (component A) and
(B) diflufenican (components B).

DETAILED DESCRIPTION OF A PREFERRED EMBODIMENT

The herbicidal compositions of the invention may comprise or else be used together with additional, further components, examples being active crop protection ingredients of other kinds and/or adjuvants customary in crop protection and/or formulating assistants. Preferred herbicidal compositions are those containing isoxaflutole and diflufenican as sole active agrochemical ingredients.

The herbicidal compositions of the invention surprisingly show not only a synergistic effect towards unwanted weed plants but also, furthermore, other special qualities: for instance, they can be applied within a broad time window in crops of useful plants against unwanted weed plants, without significant damage to the useful plants. A further surprising effect is the fact that herbicidal compositions of the invention display a synergistic effect towards weed plants which have developed resistance to HPPD inhibitors.

The herbicidal compositions of the invention can be applied in a manner known to the skilled person, as for example together (for example as a co-formulation or as a tank mix) or else a short time after one another (splitting), for example to the plants, plant parts or plant seeds or to the area on which the plants are growing. Possible, for example, is the application of the individual active ingredients or of the herbicidal compositions in two or more portions (sequential application), for example after pre-emergence applications, followed by post-emergence applications, or after early post-emergence applications, followed by applications in the middle or late post-emergence phase. Preference here is given to joint or near-synchronous application of components A and B. Also preferred is application from pre-emergence up to early post-emergence.

In the herbicidal compositions of the invention, the application rate of isoxaflutole (component A) is customarily 5 to 100 g of active ingredient (a. i.) per hectare, preferably 6 to 50 g a. i./ha, especially preferably 6 to 25 g a. i./ha. The application rate of the diflufenican herbicides (component B) is customarily 5 to 150 g of active ingredient per hectare, preferably 37.5 to 75 g a. i./ha.

At certain concentration ratios, the synergistic effect of the herbicidal compositions of the invention is particularly pronounced. However, the weight ratios of components A and B can be varied within relatively wide ranges. Generally speaking, there are 0.375 to 12 parts by weight, preferably 0.375 to 3 parts by weight, of diflufenican per part by weight of active isoxaflutole ingredient.

When the herbicidal compositions of the invention are used, a very broad spectrum of weed plants are controlled pre-emergence and post-emergence, examples being annual and perennial monocotyledonous or dicotyledonous weeds, and also unwanted crop plants. The herbicidal compositions of the invention are particularly suitable for use in crops such as cereals, maize, rice, soyabean, oilseed rape, sugarbeet, cotton and sugarcane, and for use in long-term crops, in plantations and on non-crop land. Preference is given to their use in crops of maize, cotton and soyabean. They are also very suitable for use in transgenic crops of maize, cotton and soyabean.

The present invention accordingly further provides a method for controlling unwanted plants in plant crops that is characterized in that components A and B of the herbicidal compositions of the invention are applied to the plants (e.g. weed plants such as monocotyledonous or dicotyledonous weeds or unwanted crop plants) or to the area on which the plants are growing, such application taking place jointly or separately, for example.

By unwanted plants are meant all plants that are growing at locations where they are unwanted. These may be, for example, weed plants (e.g. monocotyledonous or dicotyledonous weeds or unwanted crop plants).

Monocotyledonous weeds come, for example, from the genera *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera*. Dicotyledonous weeds come, for example, from the genera *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum, Euphorbia*.

The invention also provides for the use of the herbicidal compositions of the invention for controlling unwanted plant growth, preferably in crops of useful plants.

The herbicidal compositions of the invention can be produced by known methods, for example as mixed formulations of the individual components, optionally with further active ingredients, adjuvants and/or customary formulation assistants, these compositions being then employed in a customary way as dilutions with water, or may be produced in the form of what are called tank mixes, by joint dilution of the separately formulated or partially separately formulated individual components with water. Likewise possible is the temporally offset application (split application) of the separately formulated or partially separately formulated individual components. Another possibility is the application of the individual components or of the herbicidal compositions in two or more portions (sequential application), as for example after applications pre-emergence, followed by post-emergence applications, or after early post-emergence applications, followed by applications in the middle or late post-emergence phase. Preference here is given to the joint or near-synchronous application of the active ingredients of the respective combination.

The herbicidal compositions of the invention can also be used for controlling weed plants in crops of genetically modified plants that are either already known or are yet to be developed.

In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other special properties relate, for example, to the harvested material with regard to quantity, quality, storability, composition and specific constituents. For instance, there are known transgenic plants with an elevated starch content or altered starch quality, or with a different fatty acid composition in the harvested material. Other special properties may be tolerance or resistance to abiotic stressors, for example heat, low temperatures, drought, salinity and ultraviolet radiation.

Conventional ways of producing new plants which have modified properties in comparison to plants which have existed to date involve, for example, traditional breeding methods and the generation of mutants. Alternatively, new plants with modified properties can be generated with the aid of recombinant methods (see, for example, EP-A-0221044, EP-A-0131624). For example, there have been multiple descriptions of:

genetic modifications of crop plants for the purpose of modifying the starch synthesized in the plants (for example WO 92/11376, WO 92/14827, WO 91/19806)

transgenic crop plants which are resistant to particular herbicides of the glufosinate type (cf., for example, EP-A-0242236, EP-A-242246) or glyphosate type (WO 92/00377) or of the sulphonylurea type (EP-A-0257993, U.S. Pat. No. 5,013,659)

transgenic crop plants, for example cotton, with the ability to produce *Bacillus thuringiensis* toxins (Bt toxins), which make the plants resistant to particular pests (EP-A-0142924, EP-A-0193259)

transgenic crop plants with a modified fatty acid composition (WO 91/13972)

genetically modified crop plants with new plant constituents or secondary metabolites, for example new phytoalexins, which bring about an increased disease resistance (EPA 309862, EPA0464461)

genetically modified plants with reduced photorespiration, which feature higher yields and higher stress tolerance (EPA 0305398)

transgenic crop plants which produce pharmaceutically or diagnostically important proteins ("molecular pharming")

transgenic crop plants which feature higher yields or better quality transgenic crop plants which feature a combination, for example, of the abovementioned new properties ("gene stacking")

A large number of molecular-biological techniques by means of which new transgenic plants with modified properties can be produced are known in principle; see, for example, I. Potrykus and G. Spangenberg (eds.), Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the production of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is possible firstly to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized may be localized in any desired compartment of the plant cell. However, in order to achieve localization in a particular compartment, it is possible, for example, to join the coding region to DNA sequences which ensure localization in a particular compartment. Such sequences are known to the skilled person (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants may be plants of any desired plant species, i.e. both monocotyledonous and dicotyledonous plants.

For instance, it is possible to obtain transgenic plants whose properties are altered by overexpression, suppression or inhibition of homologous (i.e. natural) genes or gene sequences, or expression of heterologous (i.e. foreign) genes or gene sequences.

Preferably the compositions according to the invention can be used in transgenic crops which are resistant to growth regulators such as, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulphonylureas, the glyphosates, glufosinates or benzoylisoxazoles and analogous active ingredients.

On employment of the compositions of the invention in transgenic crops, the effects toward weed plants observed in other crops are often also accompanied by effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compositions of the invention for controlling weed plants in transgenic crop plants.

Preference is given to the use of the compositions of the invention in economically important transgenic crops of useful plants and ornamentals, for example of cereals (e.g. wheat, barley, rye, oats), millet/sorghum, rice, cassava and maize, or else crops of sugarbeet, cotton, soyabean, oilseed rape, potato, tomato, peas and other vegetable crops, especially in maize, cotton and soyabean.

The invention therefore also provides for the use of the compositions of the invention for controlling weed plants in transgenic crop plants or crop plants having tolerance through selective breeding.

The components A and B can be converted together or separately into customary formulations, for example for application by spraying, watering and sprinkling, such as solutions, emulsions, suspensions, powders, foams, pastes, granules, aerosols, active ingredient-impregnated natural and synthetic substances, and microencapsulations in polymeric substances. The formulations may comprise the customary auxiliaries and adjuvants.

These formulations are produced in a known manner, for example by mixing the components A and B with extenders, i.e. liquid solvents, pressurized liquefied gases and/or solid carriers, optionally with use of surfactants, i.e. emulsifiers and/or dispersants and/or foam formers.

If the extender used is water, it is also possible to use, for example, organic solvents as auxiliary solvents. Useful liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and the ethers and esters thereof, ketones, such as acetone, methyl ethyl ketone, methyl isobutyl ketone or cyclohexanone, strongly polar solvents, such as dimethylformamide or dimethyl sulphoxide, and water.

Useful solid carriers include: for example ammonium salts and ground natural minerals, such as kaolins, clays, talc, chalk, quartz, attapulgite, montmorillonite or diatomaceous earth, and ground synthetic minerals, such as finely divided silica, alumina and silicates; useful solid carriers for granules include: for example crushed and fractionated natural rocks, such as calcite, marble, pumice, sepiolite, dolomite and synthetic granules of inorganic and organic flours, and granules of organic material, such as sawdust, coconut shells, maize cobs and tobacco stalks; useful emulsifiers and/or foam formers include: for example nonionic and anionic emulsifiers, such as polyoxyethylene fatty acid esters, polyoxyethylene fatty alcohol ethers, e.g. alkylaryl polyglycol ethers, alkylsulphonates, alkyl sulphates, arylsulphonates and protein hydrolysates; useful dispersants include: for example lignosulphite waste liquors and methylcellulose.

In the formulations, it is possible to use tackifiers such as carboxymethylcellulose, natural and synthetic polymers in the form of powders, granules or lattices, such as gum arabic, polyvinyl alcohol and polyvinyl acetate, or else natural phospholipids such as cephalins and lecithins and synthetic phospholipids. Further additives may be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations contain generally between 0.1 and 95 percent by weight of components A and B, preferably between 0.5 and 90% by weight.

As such or in their formulations, the components A and B can also be used as a mixture with other agrochemically active ingredients for controlling unwanted plant growth, for example for controlling weeds or for controlling unwanted crop plants; finished formulations or tank mixes, for example, are possible.

Also possible are mixtures with other known active ingredients such as fungicides, insecticides, acaricides, nematicides, bird antifeedants, plant nutrients and soil improvers, and likewise with adjuvants and formulation assistants customary in crop protection.

The components A and B can be used as such, in the form of their formulations or the use forms prepared therefrom by further dilution, such as ready-to-use solutions, suspensions, emulsions, powders, pastes and granules. Application is typically accomplished, for example, by watering, sprinkling, spraying, broadcasting.

The components A and B can be deployed on the plants, plant parts or the area under cultivation (farmland), preferably on the green plants and plant parts, and on the farmland. One means of application is the co-deployment of the active ingredients in the form of tank mixes, by mixing the optimally formulated concentrated formulations of the individual active ingredients together in the tank with water and deploying the spray liquor obtained.

For application, the formulations present in commercial form are optionally diluted in a customary manner, for example using water in the case of wettable powders, emulsifiable concentrates, dispersions and water-dispersible granules. Preparations in the form of dusts, granules for soil application or granules for broadcasting and sprayable solutions are usually not diluted further with other inert substances prior to application.

Biological Examples

Test Conditions in the Greenhouse Trial, Herbicidal Activity Against Weed Plants Pre-Emergence Seeds of monocotyledonous and dicotyledonous weed plants and crop plants are shown in sandy loam soil in wood fibre pots, and covered with soil. The compounds of the invention, formulated in the form of wettable powders (WP) or emulsifiable concentrates (EC), are then applied to the surface of the covering earth, in the form of an aqueous suspension or emulsion, with a water application rate when converted of 600 to 800 l/ha with addition of 0.2% of wetting agent. Following the treatment, the pots are placed in a greenhouse and maintained under good growth conditions for the test plants. Visual scoring of the damage to the trial plants takes place after a trial time of 3 weeks in comparison to untreated controls (herbicidal activity in percent (%): 100% activity=plants have died; 0% activity=as control plants). The results are set out in the tables which follow.

The meanings of the abbreviations are as follows:
AMAPA (USA12001) *Amaranthus palmeri* (against HPPD-resistant species)
AMATA *Amaranthus tamariscinus*
EPHHL *Euphorbia heterophylla*
ECHCG *Echinochloa crus galli*
PHBPU *Pharbitis purpureum*
POAAN *Poa annua*
POLCO *Polygonum convolvulus*
$E^C$=Expected value according to Colby ($E^C$=A+B−A×B/100)
Δ=Difference (%) between measured value and expected value (%) (measured value minus expected value)
Evaluation:
  measured value E is greater than $E^C$:→synergism (+Δ)
  measured value E is equal to $E^C$:→additive effect
  measured value E is smaller than $E^C$:→antagonism (−Δ)

TABLE 1

| Active ingredient | Rate [g/ha] | Activity [%] against AMAPA USA12001 |
|---|---|---|
| IFT | 25 | 55% |
| DFF | 37.5 | 45% |
| IFT + DFF | 25 + 37.5 | 100% ($E^C$ = 75%, Δ = 25%) |

TABLE 2

| Active ingredient | Rate [g/ha] | Activity [%] against POAAN |
|---|---|---|
| IFT | 25 | 0% |
| DFF | 18.75 | 88% |
| IFT + DFF | 25 + 18.75 | 97% ($E^C$ = 88%, Δ = 9%) |

TABLE 3

| Active ingredient | Rate [g/ha] | Activity [%] against AMAPA USA12001 |
|---|---|---|
| IFT | 25 | 55% |
| DFF | 18.75 | 35% |
| IFT + DFF | 25 + 18.75 | 100% ($E^C$ = 71%, Δ = 29%) |

TABLE 4

| Active ingredient | Rate [g/ha] | Activity [%] against AMAPA USA12001 |
|---|---|---|
| IFT | 25 | 55% |
| DFF | 9.375 | 20% |
| IFT + DFF | 25 + 9.375 | 83% ($E^C$ =64%, Δ = 19%) |

TABLE 5

| Active ingredient | Rate [g/ha] | Activity [%] against POAAN |
|---|---|---|
| IFT | 25 | 0% |
| DFF | 9.375 | 3% |
| IFT + DFF | 25 + 9.375 | 75% ($E^C$ = 3%, Δ = 72%) |

TABLE 6

| Active ingredient | Rate [g/ha] | Activity [%] against AMAPA USA12001 |
|---|---|---|
| IFT | 13 | 15% |
| DFF | 75 | 70% |
| IFT + DFF | 13 + 75 | 99% ($E^C$ =75%, Δ = 24%) |

TABLE 7

| Active ingredient | Rate [g/ha] | Activity [%] against AMAPA USA12001 |
|---|---|---|
| IFT | 13 | 15% |
| DFF | 37.5 | 45% |
| IFT + DFF | 13 + 37.5 | 85% ($E^C$ = 53%, Δ = 32%) |

TABLE 8

| Active ingredient | Rate [g/ha] | Activity [%] against POLCO |
|---|---|---|
| IFT | 13 | 35% |
| DFF | 37.5 | 55% |
| IFT + DFF | 13 + 37.5 | 95% ($E^C$ = 71%, Δ = 24%) |

TABLE 9

| Active ingredient | Rate [g/ha] | Activity [%] against AMAPA USA12001 |
|---|---|---|
| IFT | 13 | 15% |
| DFF | 18.75 | 35% |
| IFT + DFF | 13 + 18.75 | 65% ($E^C$ = 45%, Δ = 20%) |

TABLE 10

| Active ingredient | Rate [g/ha] | Activity [%] against AMAPA USA12001 |
|---|---|---|
| IFT | 6 | 0% |
| DFF | 75 | 70% |
| IFT + DFF | 6 + 75 | 99% ($E^C$ = 70%, Δ = 29%) |

TABLE 11

| Active ingredient | Rate [g/ha] | Activity [%] against PHBPU |
|---|---|---|
| IFT | 6 | 20% |
| DFF | 75 | 70% |
| IFT + DFF | 6 + 75 | 98% ($E^C$ = 76%, Δ = 22%) |

TABLE 12

| Active ingredient | Rate [g/ha] | Activity [%] against AMAPA USA12001 |
|---|---|---|
| IFT | 6 | 0% |
| DFF | 37.5 | 45% |
| IFT + DFF | 6 + 37.5 | 73% ($E^C$ = 45%, Δ = 28%) |

TABLE 13

| Active ingredient | Rate [g/ha] | Activity [%] against PHBPU |
|---|---|---|
| IFT | 6 | 20% |
| DFF | 37.5 | 25% |
| IFT + DFF | 6 + 37.5 | 90% ($E^C$ = 4%, Δ = 50%) |

TABLE 14

| Active ingredient | Rate [g/ha] | Activity [%] against AMAPA USA12001 |
|---|---|---|
| IFT | 6 | 0% |
| DFF | 18.75 | 35% |
| IFT + DFF | 6 + 18.75 | 65% ($E^C$ = 35%, Δ = 30%) |

TABLE 15

| Active ingredient | Rate [g/ha] | Activity [%] against PHBPU |
|---|---|---|
| IFT | 6 | 20% |
| DFF | 18.75 | 3% |
| IFT + DFF | 6 + 18.75 | 60% ($E^C$ = 22%, Δ = 38%) |

TABLE 16

| Active ingredient | Rate [g/ha] | Activity [%] against EPHHL |
|---|---|---|
| IFT | 6 | 70% |
| DFF | 37.5 | 30% |
| IFT + DFF | 6 + 37.5 | 95% ($E^C$ = 79%, Δ = 16%) |

TABLE 17

| Active ingredient | Rate [g/ha] | Activity [%] against PHBPU |
|---|---|---|
| IFT | 6 | 20% |
| DFF | 9.375 | 0% |
| IFT + DFF | 6 + 9.375 | 40% ($E^C$ = 20%, Δ = 20%) |

TABLE 18

| Active ingredient | Rate [g/ha] | Activity [%] against POAAN |
|---|---|---|
| IFT | 6 | 0% |
| DFF | 9.375 | 3% |
| IFT + DFF | 6 + 9.375 | 45% ($E^C$ = 3%, Δ = 42%) |

TABLE 19

| Active ingredient | Rate [g/ha] | Activity [%] against POLCO |
|---|---|---|
| IFT | 3 | 0% |
| DFF | 37.5 | 55% |
| IFT + DFF | 3 + 37.5 | 83% ($E^C$ = 55%, Δ = 28%) |

TABLE 20

| Active ingredient | Rate [g/ha] | Activity [%] against ECHCG |
|---|---|---|
| IFT | 3 | 73% |
| DFF | 18.75 | 5% |
| IFT + DFF | 3 + 18.75 | 99% ($E^C$ = 86%, Δ = 13%) |

TABLE 21

| Active ingredient | Rate [g/ha] | Activity [%] against ECHCG |
|---|---|---|
| IFT | 3 | 73% |
| DFF | 9.375 | 5% |
| IFT +DFF | 3 + 9.375 | 97% ($E^C$ = 75%, Δ = 22%) |

TABLE 22

| Active ingredient | Rate [g/ha] | Activity [%] against AMATA |
|---|---|---|
| IFT | 3 | 10% |
| DFF | 9.375 | 83% |
| IFT +DFF | 3 + 9.375 | 100% ($E^C$ = 85%, Δ = 15%) |

The invention claimed is:

1. A synergistic composition containing, as the sole active herbicidal ingredients, (A) isoxaflutole, and (B) diflufenican.

2. The herbicidal composition according to claim 1, comprising isoxaflutole and diflufenican in a weight ratio of 1:0.375 to 12.

3. The herbicidal composition according to claim 1, comprising isoxaflutole and diflufenican in a weight ratio of 1:0.375 to 3.

4. A method for controlling one or more weed plants in one or more crops of one or more useful plants, comprising applying a herbicidal composition according to claim 1 to the weed plants, useful plants or useful plant seeds or to an area on which the crops and/or weed plants are growing.

5. A method according to claim 4, wherein the one or more useful plants are selected from the group consisting of maize, cotton and soyabean.

6. A method according to claim 4, wherein the one or more useful plants have been genetically modified.

7. A method according to claim 4, that is carried out pre-emergence or early post-emergence.

8. A method according to claim 4, that is carried out for controlling HPPD-resistant plants.

9. A method according to claim 5, wherein isoxaflutole is applied at an application rate of 5 to 100 g and diflufenican at an application rate of 5 to 150 g per hectare.

10. A method according to claim 4, wherein isoxaflutole is applied at an application rate of 6 to 25 g and diflufenican at an application rate of 37.5 to 75 g per hectare.

* * * * *